United States Patent
Aoki et al.

(10) Patent No.: US 6,617,304 B1
(45) Date of Patent: Sep. 9, 2003

(54) METHOD FOR PRODUCING MACROCYCLIC LACTONE

(75) Inventors: Takashi Aoki, Wakayama (JP); Shinji Kotachi, Wakayama (JP); Junji Koshino, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/706,732

(22) Filed: Nov. 7, 2000

(30) Foreign Application Priority Data

Nov. 8, 1999 (JP) .......................... 11-316196
Jul. 10, 2000 (JP) ........................ 2000-207804

(51) Int. Cl.$^7$ .................................. A61K 7/46
(52) U.S. Cl. ......................... 512/11; 512/25; 512/26; 549/263; 549/266; 549/267; 549/268
(58) Field of Search ................ 549/263, 266, 549/267, 268

(56) References Cited

U.S. PATENT DOCUMENTS

| | | | | |
|---|---|---|---|---|
| 2,417,151 A | * | 3/1947 | Collaud ....................... | 549/266 |
| 3,728,358 A | * | 4/1973 | Mookherjee et al. ....... | 549/271 |
| 4,110,626 A | * | 8/1978 | Katada et al. ................. | 512/2 |
| 5,693,828 A | * | 12/1997 | Belko .......................... | 549/266 |
| 5,717,111 A | * | 2/1998 | Koehler et al. .............. | 549/266 |
| 6,140,514 A | * | 10/2000 | Koehler et al. .............. | 549/266 |
| 6,222,049 B1 | * | 4/2001 | Katou et al. ................. | 549/322 |

FOREIGN PATENT DOCUMENTS

| | | |
|---|---|---|
| GB | 490044 | 8/1938 |
| JP | 41-7770 | 4/1966 |
| JP | 64-52739 | 2/1989 |
| JP | 4-46173 | 2/1992 |
| JP | 11-279172 | 10/1999 |

\* cited by examiner

*Primary Examiner*—Jill Warden
*Assistant Examiner*—Monique T. Cole
(74) *Attorney, Agent, or Firm*—Oblon, Spivak, McClelland, Maier & Neustadt, P.C.

(57) ABSTRACT

The invention discloses a method for the production of a macrocyclic lactone represented by a formula (2), which comprises subjecting a hydroxycarboxylic acid ester represented by a formula (1) to intramolecular esterification reaction.

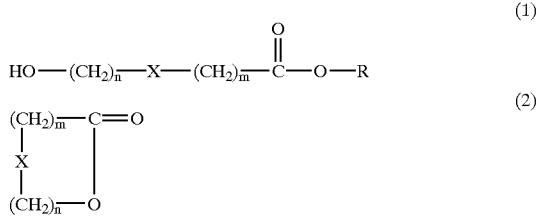

In the formulae (1) and (2), m is an integer of from 5 to 10, n is an integer wherein m+n becomes from 11 to 16, X represents —$CH_2$—, —CH=CH—, —O—, —S— or —NH—, and R represents a hydrocarbon group having from (m+n+2) to 40 carbon atoms or a group represented by —$(AO)_pR^1$ wherein AO represents an alkyleneoxy group having from 2 to 4 carbon atoms, p is average addition mole number of alkylene oxide and $R^1$ represents a hydrocarbon group having a specified number of carbon atoms so that the total number of carbon atoms of the —$(AO)_pR^1$ group becomes from (m+n+2) to 40.

17 Claims, No Drawings

METHOD FOR PRODUCING MACROCYCLIC LACTONE

BACKGROUND OF THE INVENTION

1. Field of the Invention

This invention relates to a method for the production of macrocyclic lactones which are useful as various synthetic intermediates and particularly important as ingredients of high quality perfumes.

2. Description of the Related Art

Most of macrocyclic lactones are important as fregrance raw materials having musky scent, and a large number of their production methods which use hydroxycarboxylic acid esters as the starting material have been reported. In the case of cyclopentadecanolide for example, British Patent 490,044 discloses a method in which a macrocyclic lactone is produced by intramolecular esterification from an ester of an oxycarboxylic acid with a high boiling point alcohol. According to this method, though it is described that a monohydric or polyhydric alcohol can be used as the high boiling point alcohol, only a polyhydric alcohol, glycerol, is shown in Examples. This method has problems such as reduction of yield due to decomposition of glycerol during the production of monoglyceride of 15-hydroxypentadecanoic acid to be used and the lactonization thereof.

Also, JP-B-41-7770 (the term "JP-B" as used herein means an "examined Japanese patent publication") discloses a method in which the macrocyclic lactone is obtained by distillation of hydroxycarboxylic acid ester, the alcohol moiety of which has a lower boiling point than that of macrocyclic lactone, the reaction being with adding glycerol or a liquid capable of co-distilling with lactone. In this method, the macrocyclic lactone cannot be obtained in high yield unless the reaction is carried out by continuously supplying a large amount of the liquid which is co-distilled with the macrocyclic lactone.

In addition, JP-A-64-52739 (the term "JP-A" as used herein means an "unexamined published Japanese patent application") discloses a method in which cyclopentadecanolide is produced from methyl 15-hydroxypentadecanoate containing dimethyl 1,15-pentadecandioate. But, this method causes sharp reduction of the yield when dimethyl 1,15-pentadecandioate is present in a large amount due to formation of a copolymer by transesterification with methyl 15-hydroxypentadecanoate, which accompanies distillation of methanol. Thus, not only it is necessary to remove the greater part of dimethyl 1,15-pentadecandioate before the intramolecular esterification of methyl 15-hydroxypentadecanoate, but also there is another problem in that the reaction residue becomes a highly viscous or solid substance which cannot be handled easily, due to formation of copolymers of 1,15-pentadecandioic acid, 15-hydroxypentadecanoic acid and 1,15-pentadecanediol after the reaction. Also, since diester of 1,15-pentadecandioic acid contained in the reaction residue becomes substantially unrecoverable as the result, it poses still another problem in that only about 70% of the diester can be recovered before the reaction.

SUMMARY OF THE INVENTION

The invention is a method in which a macrocyclic lactone represented by a formula (2) is produced by carrying out intramolecular esterification of a hydroxycarboxylic acid ester represented by a formula (1), and the macrocyclic lactone can be produced with high yield and high productivity by using a specified long chain alkyl ester of hydroxycarboxylic acid as the starting material.

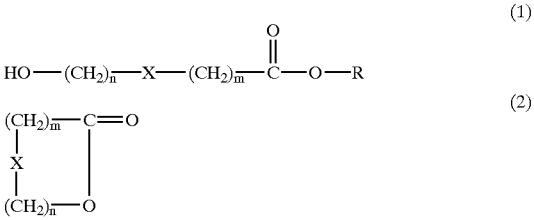

In the formulae (1) and (2), m is an integer of from 5 to 10, n is an integer wherein m+n becomes from 11 to 16, X represents $-CH_2-$, $-CH=CH-$, $-O-$, $-S-$ or $-NH-$, and R represents a hydrocarbon group having from (m+n+2) to 40 carbon atoms or a group represented by $-(AO)_pR^1$ wherein AO represents an alkyleneoxy group having from 2 to 4 carbon atoms, p is average addition mole number of alkylene oxide and $R^1$ represents a hydrocarbon group having a specified number of carbon atoms so that the total number of carbon atoms of the $-(AO)_pR^1$ group becomes from (m+n+2) to 40.

Also, the invention is a method for the production of the macrocyclic lactone of formula (2), which comprises intramolecular esterification of a hydroxycarboxylic acid or a lower alkyl (1 to 5 carbon atoms) ester thereof, obtained by partially reducing a dibasic acid represented by a formula (6) or a lower alkyl (1 to 5 carbon atoms) ester thereof, in the presence of an alcohol represented by a formula (5).

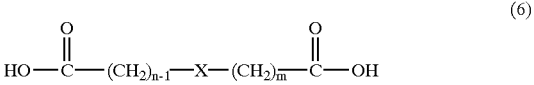

wherein X, m and n are as defined in the foregoing.

wherein R is as defined in the foregoing.

DETAILED DESCRIPTION OF THE INVENTION

According to the invention, R of the ester represented by the general formula (1) has carbon atoms of from 13 to 40 in total, and its examples include straight chain alkyl groups such as eicosyl group and octadecyl group, branched-chain alkyl groups including methyl-branched type branched-chain alkyl groups such as 3,7,11,15-tetramethyl-2-hexadecenyl group and 1-methylpentadecyl group and Guerbet alkyl type branched-chain alkyl groups such as 2-decyltetradecyl group, 2-octyldodecyl group and 2-(1,3,3-trimethylbutyl)-5,7,7-trimethyloctyl group, and polyoxyalkylene alkyl groups having an oxyalkylene addition mole number of from 1 to 12, an oxyalkylene carbon number of from 2 to 4 and an alkyl carbon number of from 1 to 16, such as $-(CH_2CH_2O)_6C_{12}H_{25}$ and $-(CH_2CH_2O)_5\{CH_2CH(CH_3)O\}_5C_{12}H_{25}$.

Among these groups, a branched-chain alkyl group or a polyoxyalkylene alkyl group represented by $-(AO)_pR^1$ (wherein AO, p and $R^1$ are as defined in the foregoing) is preferable from the viewpoint of good reaction yield and easy handling due to low melting point, more preferred is a Guerbet alkyl type branched-chain alkyl group or a polyoxyethylene alkyl group having an alkyl carbon number of from 1 to 16 and an ethylene oxide addition mole number of from 1 to 10, and particularly preferred is a Guerbet alkyl type branched-chain alkyl group.

Also, the invention can be carried out within the R carbon number of from (m+n+2) to 40, but since the alcohol formed at the time of intramolecular cyclization reaction has sufficiently higher boiling point than that of the macrocyclic lactone and can therefore be easily separated when the R carbon number is m+n+5 or more, the total carbon number of R is preferably from (m+n+5) to 40, more preferably from (m+n+5) to 36, most preferably from (m+n+5) to 32, from the viewpoint of productivity.

The ester of formula (1) to be used in the invention can be obtained for example by the following methods 1 to 3.

(Method 1) One mole of a hydroxycarboxylic acid represented by a general formula (4)

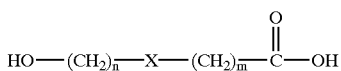
(4)

(wherein m, n and X are as defined in the foregoing) or a lower alkyl ester thereof and from 1 to 10 moles, preferably from 1 to 3 mole, of an alcohol represented by the formula (5)

 (5)

(wherein R is as defined in the foregoing) are heated at a temperature of from 30 to 300° C., preferably from 50 to 250° C., under ambient pressure to 1 kPa in the presence or absence of a catalyst, while removing the by-produced water or lower alcohol.

(Method 2) A dibasic diester represented by a formula (3)

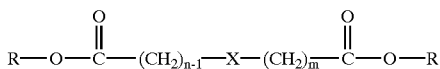
(3)

(wherein R, m, n and X are as defined in the foregoing) is partially reduced in the presence of a hydrogenation catalyst, preferably a copper-based hydrogenation catalyst, more preferably a Cu—Cr catalyst, in an amount of from 0.1 to 20% by weight, preferably from 0.2 to 10% by weight, based on the diester, under a hydrogen pressure of from 1 to 40 MPa, preferably from 5 to 30 MPa, and at a temperature of from 100 to 350° C., preferably from 150 to 300° C.

In this case, the partial reduction is carried out under the condition to suppress the formation of diol by the reduction of both ester groups of the diester as much as possible. It is an effective method to suppress the conversion to keep high selectivity, because selectivity to hydroxycarboxylic acid ester is generally reduced when conversion of diester is increased. This tendency can be found in any of known reactions such as hydrogenation and hydride reduction by a metal hydride or borane. For example, when the reduction is carried out in the presence of a Cu—Cr catalyst until conversion of the diester reaches 60% or more, 25 mole % or more of the diol is formed and yield of the hydroxycarboxylic acid ester of interest therefore is reduced. Accordingly, it is desirable to carry out the reduction by controlling the conversion of diester to 60% or less, and particularly desirable conversion of the diester is from 10 to 45%.

(Method 3) A hydroxycarboxylic acid or a lower alkyl (1 to 5 carbon atoms) ester thereof, which is obtained by partially reducing a dibasic acid represented by the general formula (6)

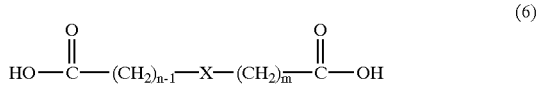
(6)

(wherein m, n and X are as defined in the foregoing) or a lower alkyl (1 to 5 carbon atoms) ester thereof in the same manner as the case of "Method 2", and an alcohol represented by the formula (5) are heated with removing the producing water or lower alcohol at a temperature of from 100 to 300° C., preferably from 150 to 250° C., under ambient pressure to 1 kPa in the presence or absence of a catalyst.

Using the thus obtained hydroxycarboxylic acid ester represented by the formula (1), its intramolecular esterification is carried out to produce the macrocyclic lactone. Among the hydroxycarboxylic acid ester production methods, the partial reduction method of the Methods 2 and 3 is particularly useful when X in the formulae (3) and (6) is —CH$_2$—, because the dibasic acid diester or dibasic acid is industrially available. It is possible to use an un-purified hydroxycarboxylic acid ester mixture containing a dibasic acid diester directly as the starting material, and such a case is desirable because the macrocyclic lactone can be produced efficiently with high yield and high productivity by a simple process without a special purification step.

In addition, since conditions of the esterification and transesterification of the Methods 1 and 3 are similar to those of the intramolecular esterification reaction for obtaining the macrocyclic lactone, it is possible to carry out the intramolecular esterification reaction without separating these two reactions in the reaction system by carrying out the esterification or transesterification in the presence of a catalyst. That is, the macrocyclic lactone of interest can be obtained by distillation when heating the reaction system is continued under a reduced pressure after the removal of water or lower alcohol in the Method 1 or 3.

A method in which the esterification or transesterification represented in the Method 1 or 3 and subsequent intramolecular esterification are carried out simultaneously in parallel is also an embodiment of the invention. That is, a method in which a macrocyclic lactone represented by the formula (2) is produced by the reaction of a hydroxycarboxylic acid or a lower alkyl (1 to 5 carbon atoms) ester thereof, which is obtained by partially reducing a dibasic acid represented by the formula (6) or a lower alkyl ester thereof, in the presence of an alcohol represented by the formula (5). In this case, from the viewpoint of yield and productivity, amount of the alcohol to be present is preferably from 0.01 to 20, more preferably from 0.1 to 10, further preferably from 0.3 to 8, most preferably from 0.5 to 5, as the [alcohol represented by the formula (5)]/[carboxyl group and/or ester group in the reaction mixture] molar ratio.

In this method, the residue after intramolecular esterification of a hydroxycarboxylic acid ester represented by the formula (1) is a low viscosity liquid or low melting point solid which can be handled easily. Also, since a dibasic acid diester, which is desired to recover and reuse, is present in this residue as a low molecular weight monomer or oligomer, it can be recovered easily in a high yield and it can be recycled directly to the reduction. Alternatively, it is possible to recover and recycle the diester as a dicarboxylic acid or a lower alkyl diester thereof by its hydrolysis or alcoholysis with lower alcohol. From the viewpoint of yield and productivity, amount of the dibasic acid diester to be contained in the un-purified hydroxycarboxylic acid ester of formula (1) is preferably 20 or less, more preferably 10 or less, most preferably 6 or less, as a molar ratio of [dibasic acid diester represented by the formula (3)]/[hydroxycarboxylic acid ester represented by the formula (1)].

In the Method 2 or 3, there is a case in which a diol formed by reduction of both of the two ester groups of diester is present. The invention can use either a hydroxycarboxylic acid ester contained mixture from which this diol is removed or a mixture containing the diol for the intramolecular esterification. Also, there is a case in which a monoester is contained in the diester, but it may be used as such. In addition, a mixture containing a polymer of hydroxycarboxylic acid esters represented by the formula (1) or of a hydroxycarboxylic acid ester with a diester or diol can also be used as such.

According to the invention, an alcohol represented by the formula (5) may be coexistent with in the hydroxycarboxylic acid ester of formula (1). Though the reaction can be carried out after removing the alcohol, it is desirable to use a mixture containing the alcohol from both yield and productivity points of view. The alcohol represented by the formula (5) may also be added in the reaction mixture. From the viewpoint of yield and productivity, preferred amount of the alcohol to be present in the reaction system is from 0.01 to 10, more preferably from 0.01 to 5, most preferably from 0.05 to 3, as a molar ratio of [alcohol represented by the formula (5)]/[hydroxycarboxylic acid ester represented by the formula (1)].

Also, when the hydroxycarboxylic acid ester of formula (1) contains a dibasic acid diester, preferred amount of the alcohol of formula (5) to be present is from 0.01 to 20, more preferably from 0.1 to 10, most preferably from 0.3 to 8, particularly preferably from 0.5 to 5, as a molar ratio of [alcohol represented by the formula (5)]/[ester group in the reaction mixture], from the viewpoint of yield and productivity.

According to the invention, the reaction can be carried out in the presence of a catalyst known as an esterification or transesterification catalyst. Preferred examples of such a type of catalyst include metal oxide catalysts such as magnesium oxide, lead oxide, zirconium oxide and zeolite, metal alkoxides such as titanium tetrabutoxide, aluminum triisopropoxide and sodium methoxide, metal hydroxides such as magnesium hydroxide, calcium hydroxide, sodium hydroxide and potassium hydroxide, metal carbonates and fatty acid metal salts such as magnesium carbonate, sodium carbonate, potassium carbonate, potassium acetate, calcium laurate and sodium stearate, and neutral or alkaline catalysts such as magnesium chloride, of which catalysts containing metals of the group II, III or IV, such as magnesium oxide and titanium tetrabutoxide, are more preferred from the viewpoint of reaction yield. Amount of the catalyst to be used can be optionally selected within the range of from 0.01 to 50% by weight based on the hydroxycarboxylic acid ester of formula (1), but is preferably from 0.1 to 20% by weight, more preferably from 0.3 to 10% by weight.

The reaction of the invention can be carried out by charging a transesterification catalyst and the hydroxycarboxylic acid ester of formula (1) at the same time and heating them at a temperature of from 100 to 350° C. under a pressure of 13 kPa or less, preferably 2.7 kPa or less, while obtaining the formed macrocyclic lactone by distillation, and the temperature range is preferably from 120 to 300° C., more preferably from 150 to 270° C., most preferably from 180 to 270° C., from the viewpoint of yield and productivity.

According to the method of the invention, like the case of the use of a glycerol ester as the ω-hydroxycarboxylic acid ester, a macrocyclic lactone can be produced with a high productivity without causing problems such as reduction of the yield by decomposition of glycerol. Also, when a hydroxycarboxylic acid ester mixture obtained by partial reduction of a diester is used, the macrocyclic lactone of interest can be produced easily and with a high yield without removing the diester from the reaction mixture prior to the intramolecular esterification reaction of hydroxycarboxylic acid ester. In addition, the unreacted diester can be recovered from the reaction residue easily with a high yield. The thus obtained macrocyclic lactone contains almost no lactone dimer and is almost free from coloration.

EXAMPLES

Determination of products by the reaction was carried out by an internal standard method of a gas chromatography.

Reference Example 1

A 10.1 g (39.0 mmol) portion of 15-hydroxypentadecanoic acid and 41.0 g (116 mmol) of 2-decyl-1-tetradecanol were put into a flask and heated at 180 to 200° C. under ambient pressure in a stream of nitrogen. When the mixture was heated for 7 hours while distilling out the by-produced water, 50.2 g of a light yellow liquid was obtained. This liquid contained 22.7 g of 2-decyl-1-tetradecyl 15-hydroxypentadecanoate (yield 98%) and 27.0 g of excess portion of 2-decyl-1-tetradecanol.

Inventive Example 1

A 32.1 g (53.9 mmol) portion of 2-decyl-1-tetradecyl 15-hydroxypentadecanoate, 38.3 g (108 mmol) of 2-decyl-1-tetradecanol and 1.5 g of magnesium oxide were put into a flask equipped with a distilling column of 2.5 cm in diameter and 15 cm in height packed with Helipack and the reaction was carried out under conditions of 230 to 250° C. and 1.3 kPa to 130 Pa while distilling out the formed cyclopentadecanolide to obtain 65.5 g of a colorless liquid distillate 5 hours thereafter. This distillate contained 12.3 g of cyclopentadecanolide (yield 95%) and 52.9 g of 2-decyl-1-tetradecanol (recovery ratio 92%).

Comparative Example 1

A 26.7 g (72.0 mmol) portion of octyl 15-hydroxypentadecanoate, 20.1 g (154 mmol) of 2-decyl-1-octanol and 1.5 g of magnesium oxide were put into the same apparatus of Inventive Example 1 and the reaction was carried out under conditions of 230 to 250° C. and 1.3 kPa to 130 Pa while distilling out the distillate to obtain 26.9 g of a colorless and transparent liquid distillate 5 hours thereafter. This contained 0.5 g of cyclopentadecanolide (yield 3%).

Inventive Example 2

A 31.4 g (60.0 mmol) portion of 3,7,11,15-tetramethyl-2-hexadecenyl 14-hydroxytetradecanoate, 5.9 g (20 mmol) of 3,7,11,15-tetramethyl-2-hexadecenol and 0.5 g of magnesium oxide were put into the same apparatus of Inventive Example 1 and the reaction was carried out under conditions of 190 to 220° C. and 1.3 kPa to 130 Pa to obtain 33.5 g of a colorless and transparent distillate 6.5 hours thereafter. This distillate contained 12.1 g of cyclotetradecanolide (yield 89%) and 18.9 g of 3,7,11,15-tetramethyl-2-hexadecenol (recovery ratio 80%).

Inventive Example 3

A 29.1 g (62.0 mmol) portion of 2-hexadecyl 14-hydroxytetradecanoate, 18.8 g (77.5 mmol) of 2-hexadecanol and 1.0 g of zinc oxide were put into the same apparatus of Inventive Example 1 and the reaction was carried out under conditions of 180 to 250° C. and 1.3 kPa to 130 Pa to obtain 41.9 g of a colorless liquid distillate 5 hours thereafter. This distillate contained 13.1 g of cyclotetradecanolide (yield 93%) and 26.4 g of 2-hexadecanol (recovery ratio 78%).

Inventive Example 4

A 24.4 g (40.1 mmol) portion of 2-decyl-1-tetradecyl 16-hydroxyhexadecanoate, 10.6 g (30.0 mmol) of 2-decyl-1-tetradecanol and 1.0 g of titanium tetrabutoxide were put into the same apparatus of Inventive Example 1 and the reaction was carried out under conditions of 190 to 230° C. and 1.3 kPa to 130 Pa to obtain 31.9 g of a colorless liquid distillate 5 hours thereafter. This distillate contained 8.7 g of cyclohexadecanolide (yield 85%) and 22 g of 2-decyl-1-tetradecanol (recovery ratio 88%).

Inventive Example 5

A 39.2 g (55.5 mmol) portion of polyoxyethylene lauryl ether {average addition mol number 6} 16-hydroxy-11-oxahexadecanoate, 13.1 g (29 mmol) of polyoxyethylene lauryl ether {average addition mol number 6} and 1.0 g of titanium tetrabutoxide were put into the same apparatus of Inventive Example 1 and the reaction was carried out under conditions of 180 to 260° C. and 2.6 kPa to 650 Pa to obtain 27.0 g of a light yellow liquid distillate 4 hours thereafter. This distillate contained 12.8 g of 11-oxa-16-hexadecanolide (yield 90%).

Comparative Example 2

A 19.8 g (72.6 mmol) portion of methyl 15-hydroxypentadecanoate, 21.0 g (228 mmol) of glycerol and 1.0 g of magnesium chloride were put into the same apparatus of Inventive Example 1 and heated to 230 to 250° C. under ambient pressure. The reaction was carried out for 1 hour, while methanol by-produced by the transesterification was distilled off from the reaction system, and then the transesterification was completed by reducing the pressure to 2.6 kPa and stirring the mixture for 30 minutes. Next, the reaction was carried out under the pressure of 650 to 130 Pa while keeping the same temperature to obtain 20.5 g of a colorless gel distillate 4 hours thereafter. However, 95% by weight of this distillate was recovered glycerol (recovery ratio 93%), and the yield of cyclopentadecanolide was 0.3 g (yield 2%).

Reference Example 2

A mixture containing 100 g (106 mmol) of di-2-decyl-1-tetradecyl pentadecanodioate and 11.6 g (32.7 mmol) of 2-decyl-1-tetradecanol and 2.6 g of Cu—Cr catalyst were put into a 500 ml capacity autoclave reactor, and hydrogenation was carried at 280° C. under a hydrogen pressure of 20 MPa to obtain a white gel (hydrogenated product) 1 hour thereafter. In addition to the diester, hydroxycarboxylic acid ester and diol, this gel contained oligomers comprised of these three compounds in a composition shown in Table 1. When a portion of the gel was decomposed with methanol and analyzed to calculate it as a composition composed of di-2-decyl-1-tetradecyl pentadecandioate, 2-decyl-1-tetradecyl 15-hydroxypentadecanoate and 1,15-pentadecanediol, it was found that the hydrogenated product has the composition shown in Table 2. The conversion of diester was 28%, and the selectivity to hydroxycarboxylic acid ester was 71%.

Composition after hydrogenated reaction

| | Amount | |
| --- | --- | --- |
| Compound name | Weight (g) | Mol (mmol) |
| Diester*1 | 63.8 | 67.5 |
| Hydroxy ester*2 | 10.2 | 17.2 |
| Diol*3 | 1.7 | 6.8 |
| Guerbet alcohol*4 | 22.0 | 62.0 |
| Others (e.g., oligomers) | 10.3 | |
| Total | 108 | |

Composition of hydrogenated product after methanolysis (per 108 g)

| Compound name | Amount Mol (mmol) |
| --- | --- |
| Diester*1 | 70.7 |
| Hydroxy ester*2 | 19.5 |
| Diol*3 | 7.9 |

*1 Di-2-decyl-1-tetradecyl pentadecandioate
*2 2-Decyl-1-tetradecyl 15-hydroxypentadecanoate
*3 1,15-Pentadecanediol
*4 2-Decyl-1-tetradecanol Inventive Example 6

A 54 g portion of the hydrogenated product obtained in Reference Example 2 and 0.2 g of magnesium oxide were put into the same apparatus of Inventive Example 1 and the reaction was carried out under conditions of 230 to 260° C. and 1.3 kPa to 130 Pa to obtain 15.2 g of a colorless liquid distillate 3 hours thereafter. This distillate contained 2.2 g of cyclopentadecanolide (yield 94%), 0.93 g of 1,15-pentadecanediol (recovery ratio 96%) and 11.3 g of 2-decyl-1-tetradecanol. The reaction residue was a light yellow liquid having a viscosity of 85 mPa·s, and 28.4 g of di-2-decyl-1-tetradecyl pentadecandioate was recovered from the residue (recovery ratio 85%).

Reference Example 3

A 150 g (499 mmol) portion of dimethyl pentadecandioate and 0.75 g of Cu—Cr catalyst were put into a 500 ml capacity autoclave reactor. A hydrogenation was carried at 260° C. for 2 hours under a hydrogen pressure of 20 MPa and then the catalyst was removed by filtration to obtain 147.1 g of a white gel (hydrogenated product). When the thus obtained reaction mixture was analyzed, it contained 91.6 g (305 mmol) of dimethyl pentadecandioate, 30.1 g (110 mmol) of methyl 15-hydroxypentadecanoate and 8.0 g (32.7 mmol) of 1,15-pentadecanediol. Also, when the reaction mixture was subjected to methanolysis and then analyzed, it was found that the hydrogenated product contained oligomers including 9.6 mmol equivalent of 15-hydroxypentadecanoic acid.

Inventive Example 7

A 20 g portion of the hydrogenated product obtained in Reference Example 3, 40 g of 2-octyl-1-dodecanol and 0.5 g of titanium tetrabutoxide were put into the same apparatus of Inventive Example 1 and the reaction was carried out for 10 hours under ambient pressure to 270 Pa at 150 to 230° C. to obtain 18.8 g of a colorless liquid distillate. This distillate contained 3.6 g of cyclopentadecanolide (yield 92%). The reaction residue was a light yellow liquid, and 30.5 g of di-2-octyl-1-dodecyl pentadecandioate was recovered from the residue (recovery ratio 83%).

Comparative Example 3

A 20 g portion of the hydrogenated product obtained in Reference Example 3 and 0.5 g of titanium tetrabutoxide were put into the same apparatus of Inventive Example 1, and when the reaction was carried out under ambient pressure to 270 Pa and at 150 to 230° C., 0.4 g of methanol was found in the distillate 4 hours thereafter, but the mixture in the flask became white solid at room temperature and cyclopentadecanolide was not obtained.

Inventive Example 8

A 13.1 g (48.1 mmol) portion of methyl 15-hydroxypentadecanoate, 45.1 g (100 mmol) of polyoxyethylene lauryl ether {average addition mol number 6} and 1.0 g of magnesium oxide were put into the same apparatus of Inventive Example 1, and the reaction was carried out under ambient pressure to 1.3 kPa and at 190 to 245° C. for 3 hours, while distilling out methanol, and then under 53 Pa and at 160 to 260° C. to obtain 19.5 g of a colorless to light yellow liquid. This distillate contained 11.0 g of cyclopentadecanolide (yield 95%).

The entire disclosure of each and every foreign patent application from which the benefit of foreign priority has been claimed in the present application is incorporated herein by reference, as if fully set forth.

What is claimed is:

1. A method for producing a macrocyclic lactone represented by a formula (2), which comprises subjecting a hydroxycarboxylic acid ester represented by a formula (1) to intramolecular esterification:

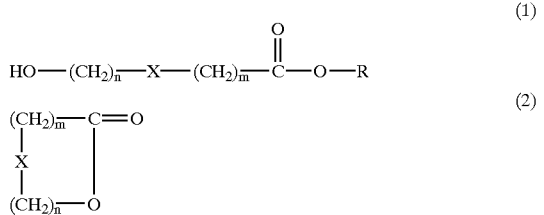

wherein m is an integer of from 5 to 10, n is an integer wherein m+n becomes from 11 to 16, X represents —$CH_2$—, —CH=CH—, —O—, —S— or —NH—, and R represents a hydrocarbon group having from (m+n+2) to 40 carbon atoms or a group represented by —$(AO)_pR^1$ wherein AO represents an alkyleneoxy group having from 2 to 4 carbon atoms, p is average addition mole number of alkylene oxide and $R^1$ represents a hydrocarbon group having a specified number of carbon atoms so that the total number of carbon atoms of the —$(AO)_pR^1$ group becomes from (m+n+2) to 40.

2. A method for producing a macrocyclic lactone represented by a formula (2), which comprises carrying out intramolecular esterification of a hydroxycarboxylic acid or a lower alkyl ester thereof, obtained by partially reducing a dibasic acid represented by a formula (6) or a lower alkyl ester thereof, in the presence of an alcohol represented by a formula (5):

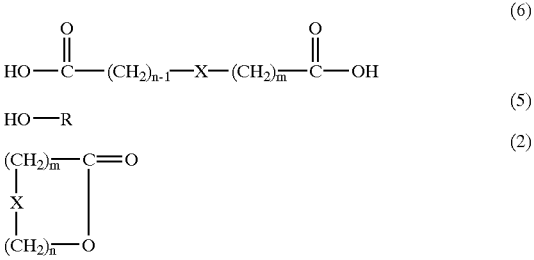

wherein m is an integer of from 5 to 10, n is an integer wherein m+n becomes from 11 to 16, X represents —$CH_2$—, —CH=CH—, —O—, —S— or —NH—, and R represents a hydrocarbon group having from (m+n+2) to 40 carbon atoms or a group represented by —$(AO)_pR^1$ wherein AO represents an alkyleneoxy group having from 2 to 4 carbon atoms, p is average addition mole number of alkylene oxide and $R^1$ represents a hydrocarbon group having a specified number of carbon atoms so that the total number of carbon atoms of the —$(AO)_pR^1$ group becomes from (m+n+2) to 40.

3. The method for producing a macrocyclic lactone according to claim 2, wherein molar ratio of the alcohol of formula (5) to the total of carboxyl group and ester group in the reaction mixture is from 0.01 to 20.

4. The method of claim 1, wherein R is selected from the group consisting of eicosyl, octadecyl, 3,7,11,15-tetramethyl-2-hexadecenyl, 1-methylpentadecyl, 2-decyltetradecyl, 2-octyldodecyl, 2-(1,3,3-trimethylbutyl)-5,7,7-trimethyloctyl, —$(CH_2CH_2O)_6C_{12}H_{25}$ and —$(CH_2CH_2O)_5(CH_2CH(CH_3)O)_5C_{12}H_{25}$.

5. The method of claim 1, wherein R is selected from the group consisting of 3,7,11,15-tetramethyl-2-hexadecenyl, 1-methylpentadecyl, 2-decyltetradecyl, 2-octyldodecyl, 2-(1,3,3-trimethylbutyl)-5,7,7-trimethyloctyl, —$(CH_2CH_2O)_6C_{12}H_{25}$ and —$(CH_2CH(CH_2CH(CH_3)O)_5 C_{12}H_{25}$.

6. The method of claim 1, wherein R is selected from the group consisting of 2-decyltetradecyl, 2-octyldodecyl, 2-(1,3,3-trimethylbutyl)-5,7,7-trimethyloctyl, —$(CH_2CH_2O)_6 C_{12}H_{25}$ and —$(CH_2CH_2O)_5(CH_2CH(CH_3)O)_5C_{12}H_{25}$.

7. The method of claim 1, wherein R is selected from the group consisting of 2-decyltetradecyl, 2-octyldodecyl and 2-(1,3,3-trimethylbutyl)-5,7,7-trimethyloctyl.

8. The method of claim 1, wherein X is —$CH_2$—.

9. The method of claim 1, further comprising distilling said macrocyclic lactone of formula 2.

10. The method of claim 1, further comprising using said macrocyclic lactone in a perfume.

11. The method of claim 2, wherein R is selected from the group consisting of eicosyl, octadecyl, 3,7,11,15-tetramethyl-2-hexadecenyl, 1-methylpentadecyl, 2-decyltetradecyl, 2-octyldodecyl, 2-(1,3,3-trimethylbutyl)-5,7,7-trimethyloctyl, —$(CH_2CH_2O)_6C_{12}H_{25}$ and —$(CH_2CH_2O)_5(CH_2CH(CH_3)O)_5C_{12}H_{25}$.

12. The method of claim 2, wherein R is selected from the group consisting of 3,7,11,15-tetramethyl-2-hexadecenyl, 1-methylpentadecyl, 2-decyltetradecyl, 2-octyldodecyl, 2-(1,3,3-trimethylbutyl)-5,7,7-trimethyloctyl, —$(CH_2CH_2O)_6C_{12}H_{25}$ and —$(CH_2CH_2O)_5(CH_2CH(CH_3)O)_5C_{12}H_{25}$.

13. The method of claim 2, wherein R is selected from the group consisting of 2-decyltetradecyl, 2-octyldodecyl, 2-(1, 3,3-trimethylbutyl)-5,7,7-trimethyloctyl, —$(CH_2CH_2O)_6$ $C_{12}H_{25}$ and —$(CH_2CH_2O)_5(CH_2CH(CH_3)O)_5C_{12}H_{25}$.

14. The method of claim 2, wherein R is selected from the group consisting of 2-decyltetradecyl, 2-octyldodecyl and 2-(1,3,3-trimethylbutyl)-5,7,7-trimethyloctyl.

15. The method of claim 2, wherein X is —$CH_2$—.

16. The method of claim 2, further comprising distilling said macrocyclic lactone of formula 2.

17. The method of claim 2, further comprising using said macrocyclic lactone in a perfume.

* * * * *

UNITED STATES PATENT AND TRADEMARK OFFICE
CERTIFICATE OF CORRECTION

PATENT NO. : 6,617,304 B1
DATED : September 9, 2003
INVENTOR(S) : Aoki et al.

It is certified that error appears in the above-identified patent and that said Letters Patent is hereby corrected as shown below:

<u>Title page</u>
Item [*] Notice, should read:
-- [*]  Notice:   Subject to any disclaimer, the term of this patent is extended or adjusted under 35 U.S.C. 154(b) by 347 days. --

Signed and Sealed this

Second Day of November, 2004

JON W. DUDAS
*Director of the United States Patent and Trademark Office*